United States Patent [19]
Yoshida et al.

[11] Patent Number: 5,891,682
[45] Date of Patent: Apr. 6, 1999

[54] RADIATION DOSIMETER AND METHOD OF MAKING AND USING

[75] Inventors: Hiroko Yoshida; James D. Regan, both of Melbourne Beach, Fla.

[73] Assignee: Florida Institute of Technology, Melbourne, Fla.

[21] Appl. No.: 851,634

[22] Filed: May 6, 1997

Related U.S. Application Data

[60] Provisional application No. 60/016,892 May 6, 1996.

[51] Int. Cl.$^6$ .............................. C12Q 1/68; C12P 19/34; C12M 1/00; C07H 21/04

[52] U.S. Cl. ........................... 435/91.2; 435/6; 435/91.1; 435/287.2; 436/94; 536/23.1; 536/24.3; 536/24.33; 536/25.3

[58] Field of Search .............................. 435/6, 91.1, 91.2, 435/183, 287.2; 536/23.1, 24.3, 24.33, 25.3; 436/94

[56] References Cited

PUBLICATIONS

"*DNA as a Solar Dosimeter in the Ocean,*" J.D. Regan, et al., Photochemistry and Photobiology, vol. 56, No. 1, pp. 35–42.

"*Journal of Photochemistry and Photobiology,*" B. Biology, James D. Regan, et al., Department of Biological Sciences and Claude Pepper Institute, Florida Institute of Technology, Melbourne, Florida, Published Dec. 11, 1995, pp. 57–61.

*Primary Examiner*—Bradley L. Sisson
*Attorney, Agent, or Firm*—Allen, Dyer, Doppelt, Milbrath & Gilchrist, P.A.

[57] ABSTRACT

A device for measuring a total dose of biologically effective radiation is provided, in a specific embodiment, for measuring ultraviolet B radiation (UVB) in the wavelength range of 290–400 nm. X-radiation and high-energy particle radiation are also measurable with this device. The device includes a sample of DNA dried onto a plastic film, and the analysis method includes assaying for damage with the use of polymerase chain reaction and fluorescence techniques. The damage to the DNA is correlatable with dosage via a comparison with standardized calibration data.

21 Claims, 13 Drawing Sheets

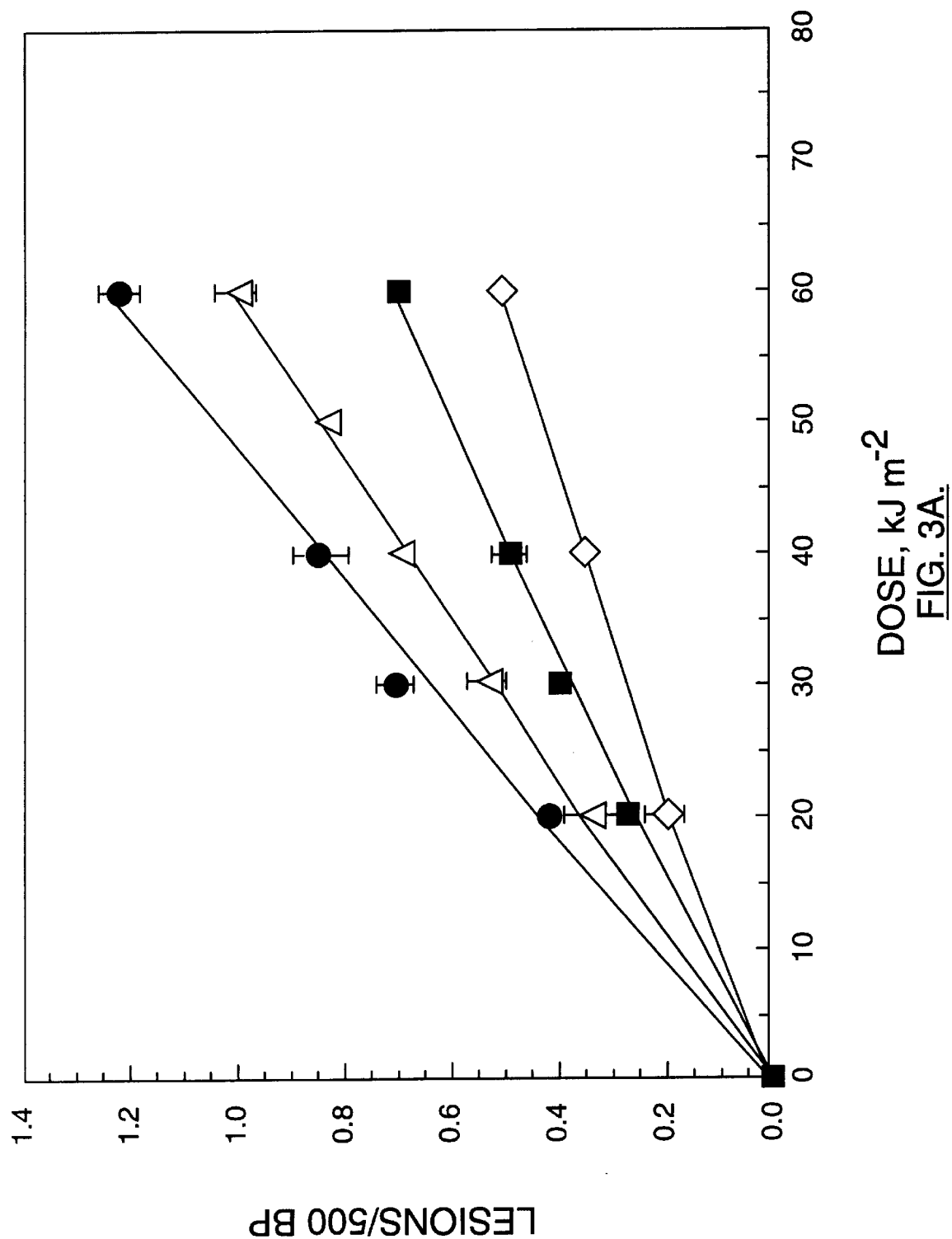

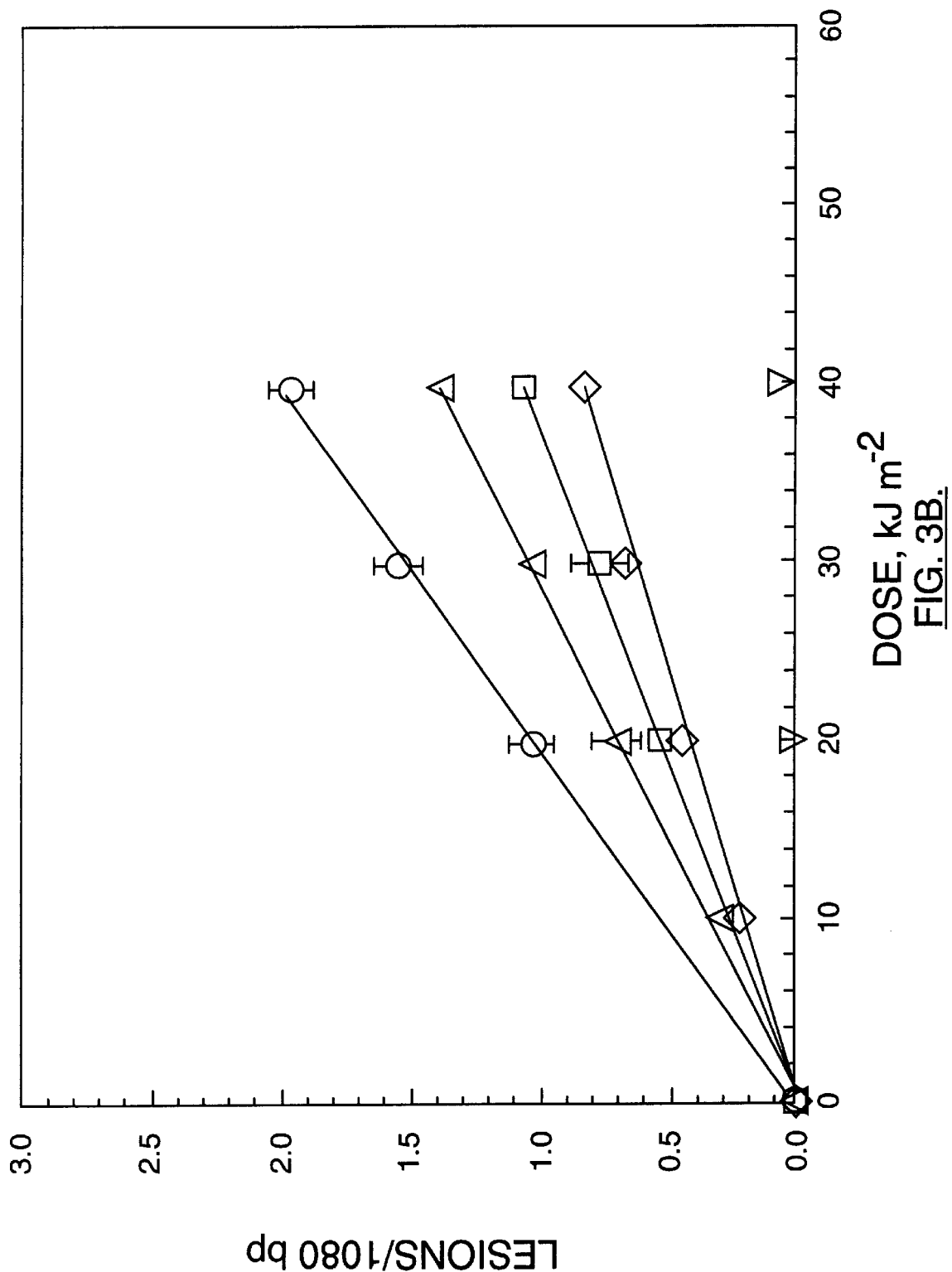

230 bp (7401-7630)
 Primer 2  GGTTATCGAA ATCAGCCACA GCGCCT
 Primer 0  TGGGATCAGC GCAGCCGGAT ACCGT

500 bp (7131-7630)
 Primer 2  GGTTATCGAA ATCAGCCACA GCGCC
 Primer 1  GATGAGTTCG TGTCCGTACA ACTGG

1080 bp (6551-7630)
 Primer 2  GGTTATCGAA ATCAGCCACA GCGCC
 Primer 4  ATACCATG ACCGGTGAAG CCTTC

2240 bp (5391-7630)
 Primer 2  GGTTATCGAA ATCAGCCACA GCGCC
 Primer 3  CTGACGTTAC TGACGTGGTG CCAGC

4000 bp (3631-7630)
 Primer 2  GGTTATCGAA ATCAGCCACA GCGCCT
 Primer 5  AACACGCAGC TGCAGAGCGC CATTG

FIG. 10.

RADIATION DOSIMETER AND METHOD OF MAKING AND USING

CROSS-REFERENCE TO RELATED APPLICATION

This application claims priority from provisional application Serial No. 60/016,892, "Radiation Dosimeter and Method," filed May 6, 1996.

BACKGROUND OF THE INVENTION

1. Field of the Invention

The present invention relates to devices and methods for quantifying a radiation dosage, and, more particularly, to devices and methods for quantifying a dosage of ultraviolet and x-radiation and high-energy particle radiation.

2. Description of Related Art

As it is known that certain wavelengths of radiation can be harmful to living creatures, it is desirable to be able to measure a "local dose" of incident radiation in order to monitor incident radiation. Physical photometers measure an irradiance, or instantaneous rate; a biologically effective dose must be obtained from these data by integrating with a DNA absorption spectrum. This total dose is important for correlating with a biological response such as cell mortality, mutation, or carcinogenesis.

The biologically effective UV radiation that reaches the Earth's surface is generally in the range of 290–320 nm, and it is known that, presumably owing to the destruction of the Earth's ozone layer, the incident amount in this range has been increasing with time.

It is known to use deoxyribonucleic acid (DNA) as a molecular dosimeter for ultraviolet radiation, since total dose data are provided, and since the peak of DNA absorption is approximately 260 nm. It is also advantageous to use DNA, because the principal target for UV damage in living organisms is DNA.

Naked DNA is known to provide "worst-case" damage data, since DNA in vivo is usually afforded some protection by surrounding structures such as nucleoproteins and can be repaired by intracellular mechanisms. Therefore, a DNA dosimeter records the maximum UV damage sustainable by such a molecule at the place and time it is exposed.

It has been known to use radioactive $^3$H-labeled DNA as a solar dosimeter in the ocean; however, a problem associated with this technique is the potential for introducing an undesirable material into the environment.

van Houten et al. (*Amplifications* 10, 10–17, 1993) have quantified the average lesion frequency in UV-irradiated *E. Coli* lacZ and lacI genes with the polymerase chain reaction.

It is also known that x-radiation and high-energy particle radiation cause damage to DNA.

At present there exists no convenient, portable, inexpensive, safe, compact device and method for measuring a biologically effective dosage of radiation, specifically, a dosage of UV and x-radiation and high-energy particle radiation, incident upon a selected object or area over a desired time period.

SUMMARY OF THE INVENTION

It is therefore an object of the present invention to provide a device and method for measuring a radiation dosage incident upon a selected object or area.

It is an additional object to provide such a device that is compact, portable, and inexpensive to use and analyze.

It is another object to provide a method of analyzing a detector substance in the device to yield dosage information.

It is a further object to provide such a device that can measure a local dose of solar ultraviolet radiation, in particular, solar ultraviolet B radiation.

It is yet another object to provide such a device that is operable in extremes of environmental conditions, including under water.

These and other objects are attained with the device and method of the present invention. The device is a dosimeter for measuring a radiation dosage in a predetermined wavelength range. The dosimeter comprises a first supporting structure, such as a film, and a quantity of detection DNA adhered to a first side thereof. The DNA preferably has a known number and sequence of base pairs and a vulnerability to radiation in the predetermined wavelength range. These characteristics enable damage to be quantified after exposure for a period of time.

Preferably the DNA/film dosimeter is encased in a housing at least one face of which is transparent to radiation in the predetermined wavelength range.

Also preferably the dosimeter further comprises a control segment comprising a second supporting structure, which may comprise a portion of the first supporting structure, and a quantity of control DNA adhered thereto. The control DNA comprises a DNA essentially identical in type to the detection DNA. Means are provided for shielding the control segment from impinging radiation in the predetermined wavelength range.

Exposure of the detection DNA to radiation in the predetermined wavelength range produces quantifiable damage that is indicative of the radiation dosage, thereby enabling the DNA to serve as a dosimeter. The small amounts of DNA required for subsequent quantification (typically in the tens of nanogram range) permits the dosimeter to be small, portable, and easy to use.

The method of the present invention for making the dosimeter comprises the steps of adhering a quantity of detection DNA to a first side of the supporting structure and of adhering a quantity of control DNA to a first side of a second supporting structure. Next the control DNA is covered with a shield placed in protecting relation to the control DNA, the shield being impervious to radiation in the predetermined wavelength range. Preferably, the first and the second shielded supporting structures with the DNA adhered thereto are packaged into a device that is affixable to a user, or to a site at which dosage information is desired to be collected.

The method of the present invention for obtaining radiation dosage data comprises the steps of exposing a known quantity of detection DNA to an environment for a measured time span, the DNA vulnerable to radiation in the predetermined wavelength range and having a known number and sequence of base pairs. A region of the exposed DNA is then amplified, and a lesion frequency within the exposed DNA is determined from the resulting amplified exposed DNA region.

A set of dose-response data are preferably obtained prior to performing the dosage measurement of the present invention. These data are calculated by subjecting a known quantity of calibration DNA to a known dose of radiation within the predetermined wavelength range, the calibration DNA essentially identical in type to the detection DNA.

The dose of biologically effective radiation is determined by comparing the determined lesion frequency with the predetermined set of calculated dose-response data.

Preferably, the method also includes exposing a shielded known quantity of control DNA to the environment at the same time during which the detection DNA is exposed. The control DNA is preferably essentially identical in type to the detection DNA. The control DNA is then subjected to the same amplification, lesion-frequency-determining, and dose-determining steps as the detection DNA.

The features that characterize the invention, both as to organization and method of operation, together with further objects and advantages thereof, will be better understood from the following description used in conjunction with the accompanying drawings. It is to be expressly understood that the drawings are for the purpose of illustration and description and are not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

FIG. 3A plots the average lesion frequency for a 500-bp segment as a function of incident dose applied with the solar UVB simulator.

FIG. 3B plots the average lesion frequency as for FIG. 3A, for a 1080-bp segment.

FIG. 10 provides the sequences for the primer combinations for (A) 230-bp; (B) 500-bp; (C) 2240-bp; (D) 1080-bp; and (E) 4000-bp PCR products.

DETAILED DESCRIPTION OF THE PREFERRED EMBODIMENTS

A description of the preferred embodiments of the present invention will now be presented with reference to FIGS. 1–10. A portion of the method of the present invention has been disclosed in a publication of the inventors, "DNA UVB Dosimeters" (J. Photochem. Photobiol. B: Biology 31, 57–61, 1995), the enntire disclosure of which is incorporated herein by reference. While the discussion to follow details a UVB dosimeter, it is to be understood that this is not intended to be limiting, as the other types of radiation discussed above are intended to be subsumed within the scope of this invention.

Assembly of the Dosimeter

Figure 1A:
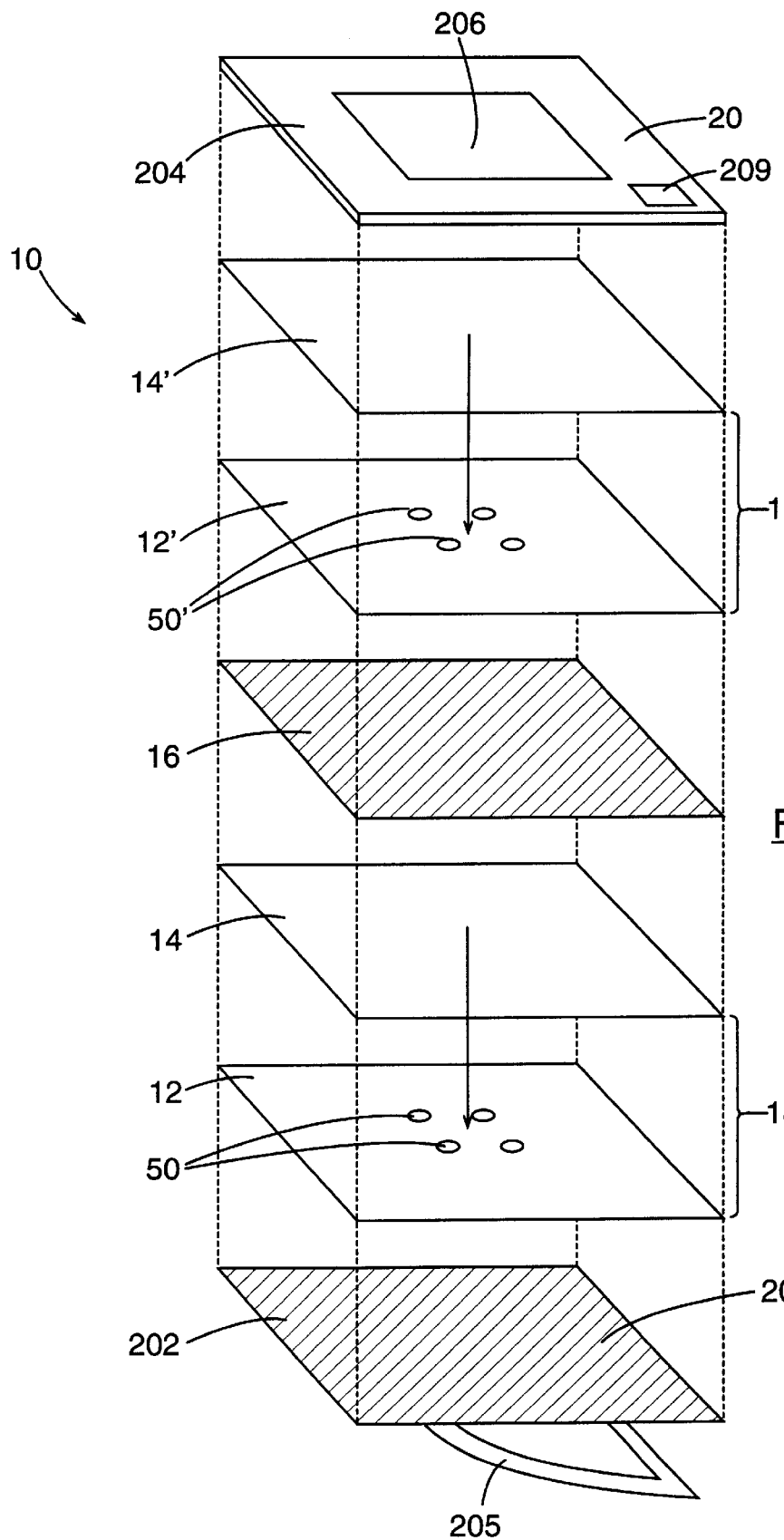
FIG. 1A is an exploded perspective view of the dosimeter of the present invention.
Figure 1B:
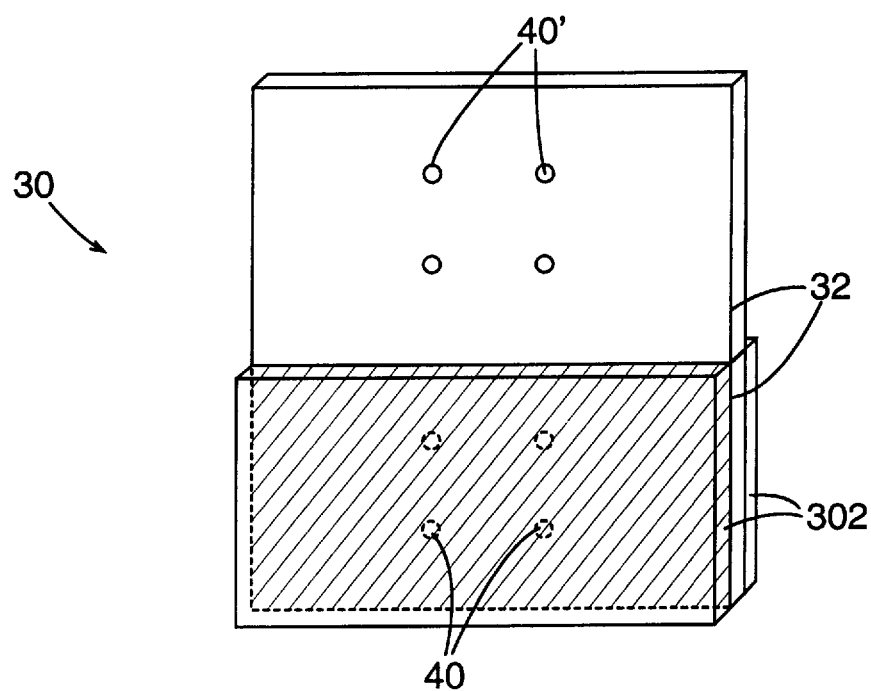
FIG. 1B is a plan view of an alternate embodiment of the dosimeter for use under water.
Figure 8:
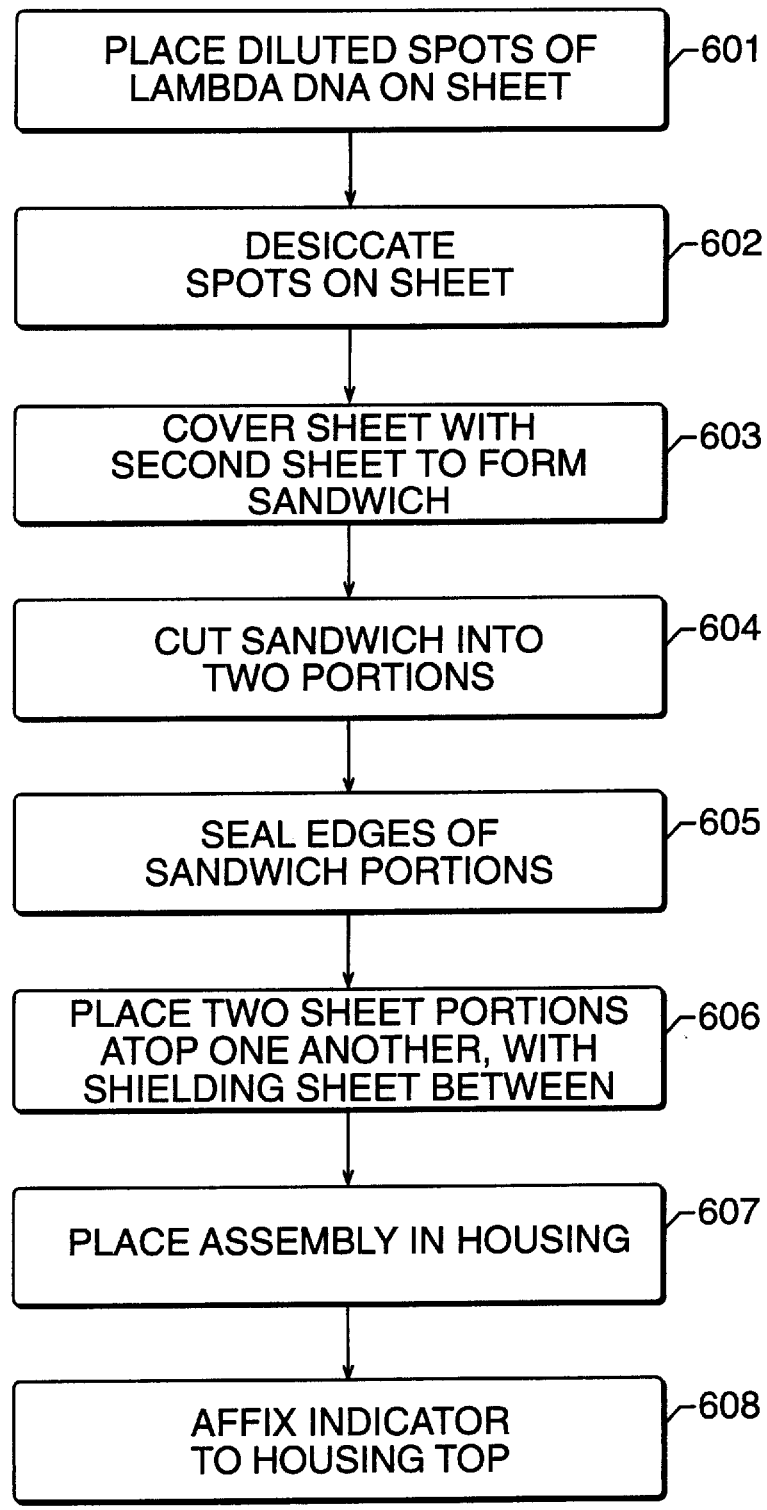
FIG. 8 is a flow chart illustrating the method of making the dosimeter.

The device, a first embodiment of which is shown in FIG. 1A, is assembled as outlined in FIG. 8, and comprises a dosimeter 10 for measuring an incident dosage of UVB radiation. The dosimeter 10 comprises a first support sheet 12 of ACLAR™ UV-transparent plastic film (Allied Signal, Pottsville, Pa.), which transmits 92% of light above 250 nm. Onto this sheet 12 are placed a plurality of spots 50 of λ DNA (Block 601) (New England Biolabs, 500 μg/mL) that has been diluted with TE buffer [10 mM Tris-HCl (pH 8.0) and 1 mM EDTA] to a desired concentration, as measured with a Spectronic 601 UV spectrophotometer (Milton Roy, Rochester, N.Y.). In a preferred embodiment, a total of 8 spots 50, each comprising 5 μl (50 ng) of the λ DNA, are placed on the support sheet 12.

λ DNA is beneficial for this purpose because its sequence is precisely known, which is necessary for the subsequent damage analysis. In addition, there is a diverse selection of lengths available in amplification products, which in turn provides a variety of exposure times: A longer segment, having a higher number of UV-induced lesions (on average), can be used for shorter exposure times; a shorter segment, having a smaller number of UV-induced lesions (on average), can be used for longer exposure times. This particular DNA is not meant to be limiting, however, and the invention disclosed herein contemplates the use of other radiation-vulnerable nucleic acids as well.

The sheet 12 having the DNA spots 50 thereon is then placed in a desiccator having preheated silica gel therein and left for 12–15 hours (e.g., overnight) at 40° C. (Block 602).

After drying, a second, covering sheet 14 of ACLAR™ film is placed in covering relation to the support sheet 12 and rubbed to promote the sheets' 12,14 adherence together, the DNA spots 50 thereby sandwiched therebetween (Block 603).

The dosimeter 10 is then assembled by cutting the sheet/DNA/sheet 12/50/14 sandwich into two portions, each containing 4 DNA spots 50 (Block 604). The dosage-measuring component reference numerals will now be primed to distinguish them from the control components, for example, the detection DNA spots 50' and control DNA spots 50.

In a preferred embodiment, a sealing means such as a nonreactive silicone 18,18' is applied to the edges of the control sheet/DNA/sheet 12/50/14 and dosage-measuring 12'/50'/14' sandwiches to provide protection from fluid intrusion (Block 605). The effect of silicone 18 on the PCR product was tested and found not to interfere with the PCR amplification process.

The dosimeter 10 additionally comprises a housing 20 having a bottom section 202 and a top section 204. The bottom section 202 may have means for attaching to an object or living being, such as a clip 205, for ease of use, as are common in X-ray film badges. The top section 204 has a portion 206 situated above the detection DNA spots 50' that is transparent to wavelengths in the range of interest, here generally 290–320 nm, and also to high-energy particles desired to be measured. Alternatively, the top section 204 may have an opening sufficiently large to permit the DNA spots 50' exposure to impinging radiation and particles.

In exemplary embodiments a radiation badge or a 5 cm×5 cm slide mount may be used as a housing.

An assembly is formed by placing between the control sandwich 12/50/14 and the detection sandwich 12'/50'/14' a shielding sheet 16, for example, comprising black plastic, that is impervious to radiation in the wavelength range of interest (and to high-energy particles desired to be measured with proper shielding) (Block 606). The dosimeter 10 is assembled by placing the assembly between the housing top 204 and bottom 202 sections (Block 607), with the control sandwich 12/50/14 adjacent the housing bottom section 202.

In an alternate embodiment wherein silicone sealant is not used, the housing 20 is preferably watertight.

In a particular embodiment the dosimeter 10, owing to its design as compared with previously known dosimeters, can be made very small, permitting portability, inconspicuousness, and ease of use. Such a small size also permits the dosimeter 10 to be used on animals that might not otherwise tolerate wearing a large, bulky, and/or heavy object.

Affixed to a corner of the housing top 204 in a particular embodiment is a piece of polysulfone film 209, which darkens upon exposure to UVB radiation (Block 608). The polysulfone film 209 is used as an indicator, whereby a darkened condition indicates that the dosimeter 10 has already been exposed to UVB radiation and should be discarded.

In an alternate embodiment, such as for underwater use, the dosimeter 30 (FIG. 1B) comprises a unitary ACLAR™ film 32 for two-sided collection, whereto the DNA detection and control spots 40',40 are adhered. The control spots 40 are shielded, for example, by a radiation-impervious layer, such as a black tape 302 or black paint placed in covering relation to the control spots 40 on both sides of the film 32. This arrangement permits collection of dose information incident on the dosimeter 30 over 360°.

Calibrations of the Dosimeter

The dosimeter 10 is irradiated under controlled conditions in a solar UV simulator for a series of times, the dose rate being measured by a photometer. In particular, a Jagger meter is covered with one layer of ACLAR™ film and two layers of 0.13-mm-thick KODACEL (Eastman Kodak, Rochester, N.Y.). The thus-filtered Jagger meter is placed in a solar UVB simulator, comprising two FS40 lamps (Westinghouse, Pittsburgh, Pa.) in parallel alignment on the top to mimic the UVB region of the solar spectrum. UV irradiance (J m$^{-2}$ sec$^{-1}$) is converted from current ($\mu$amp). The solar simulator exhibits a spectrum between 290 and 400 nm, with a maximum at 315 nm. The two layers of KODACEL film is replaced every 16 h of UV irradiation, as it is solarized with time.

For field testing the DNA dosimeter is placed vertically at 1.5 m above the ground facing south, and the ground around the site was covered with grass (low albedo), and no shadowing or shielding was observed during testing.

The dosimeter 10 is also exposed to known dose rates of x rays and $^{60}$Co, and then calibration is performed by multiplying the known dose rate by exposure time. For dosages of high-energy particles, an accelerator is used for calibration.

For irradiation of aqueous λ DNA, solutions (5 ng $\mu$l$^{-1}$) are placed into wells (3 mm diam.×2 mm depth) in a acrylic block (10×8×1 cm) and irradiated with a germicidal lamp (primary emission at 254 nm) and with a solar UVB simulator. ACLAR™ film is placed over the entire block for the irradiation with the solar simulator. After the irradiation, 6 $\mu$l of irradiated λ DNA solution (5 ng $\mu$l$^{-1}$) from three individual holes is transferred into PCR tubes for comparison with a 30-ng dried DNA dosimeter.

For irradiation of standard dried DNA through MYLAR film, in addition to the two layers of KODACEL film, a layer of MYLAR film is placed over the standard, dried DNA (30 ng). The MYLAR film blocks UV radiation below 315 nm. Calibration is then accomplished by placing a layer of ACLAR™ film, two layers of KODACEL, and a layer of MYLAR over the Jagger meter.

The DNA spots 50 are then analyzed as will be described below to correlate the known dose rate with DNA damage.

Analysis of the Irradiated Dosimeter

Figure 9:
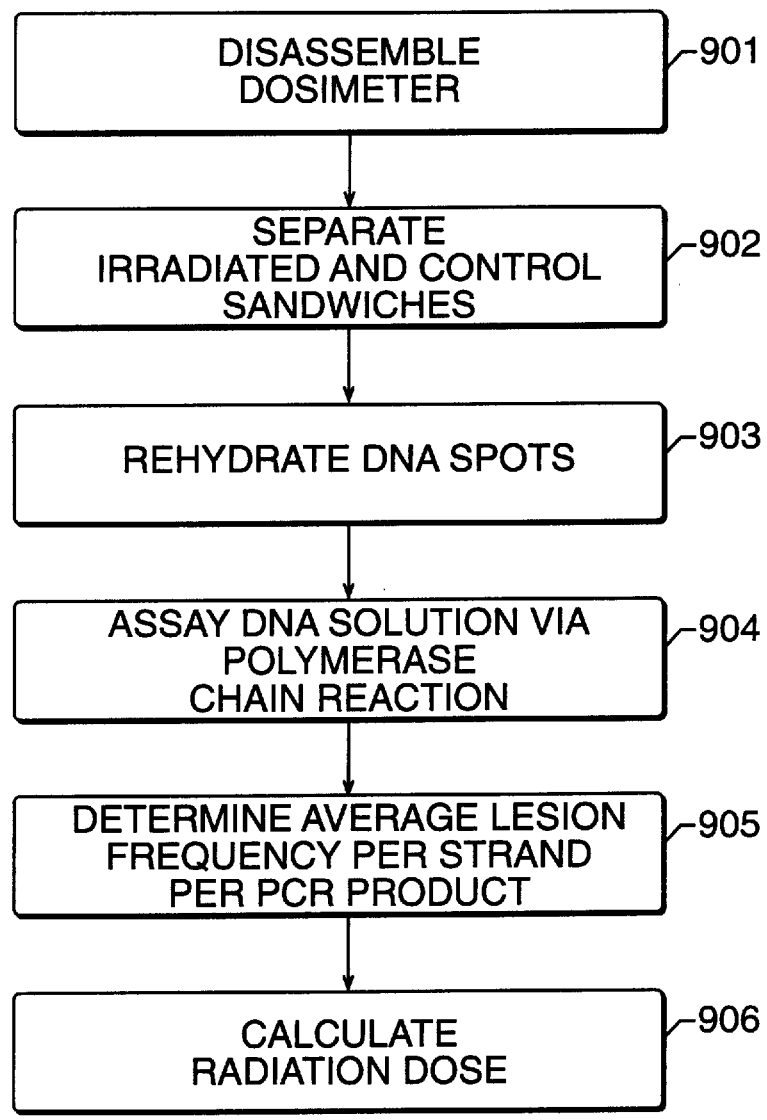
FIG. 9 is a flow chart illustrating the method of analyzing the dosimeter to yield dosage data.

As shown in the flow chart of FIG. 9, the dosimeter 10 is disassembled (Block 901), and the control and irradiated covering sheet/DNA/support sheet sandwiches 12/50/14 and 12'/50'/14' are separated (Block 902) to expose the DNA spots 50,50'. The DNA is then rehydrated (Block 903) in 4 $\mu$l of distilled, sterilized water, with the solution resulting from three washes of the two sheets comprising 24 $\mu$l volume for each of the irradiated and control samples.

The solutions are placed in PCR tubes (Perkin Elmer, Foster City, Calif.) for a polymerase chain reaction (PCR) assay (Block 904), which has already been described (J. D. Regan and H. Yoshida, *J. Photochem. Photobiol. B: Biology* 31, 57–61, 1995). This technique amplifies specific genomic regions in template DNA only if the DNA is undamaged, that is, if there are no areas having intrastrand dimers, breakage, or cross-linking. A dose-response curve can then be obtained (Block 905) by plotting the average lesion frequency per strand per PCR product as a function of dose. A solution of fluorescent dye that binds to A-T-rich regions of double-stranded DNA is used to quantify (Block 906) PCR products, which is indicative of dose.

The combination of the PCR and fluorescence assays is known to be advantageous over other techniques in its nonreliance on radiolabeled DNA, its speed, and its sensitivity.

The specific protocol is carried out as follows: Mix the PCR reagents in a total volume of 50 $\mu$l according to Table 1.

TABLE 1

Volumes of PCR Reagents Used for Protocol

|  | Volume ($\mu$l) | Final Concentration |
| --- | --- | --- |
| H$_2$O | 14.15 |  |
| 10X Buffer[a] | 5 |  |
| DNTP (dATP, dCTP, dGTP, dTTP)[b] | 4 | 200 $\mu$M each |
| Primer A[c] | 1.3 | 1 $\mu$M |
| Primer B[c] | 1.3 | 1 $\mu$M |
| Taq polymerase[d] | 0.25 | 2.5 units |
| Lambda DNA[e] | 24 | 50 ng |
| Total | 50 |  |

[a]GibcoBRL, Grand Island, NY.
[b]Pharmacia Biotech, Piscataway, NJ.
[c]Bio-Synthesis, Inc., Lewisville, TX.
[d]Promega, Madison, WI.
[e]New England BioLabs, Inc., Beverly, MA.

Generally 16 PCR cycles are carried out.

Five Primer A/B combinations have been detailed, although this is not meant to be limiting (see FIG. 10 for primer sequences). A Primer 0/Primer 2 combination produces a 230-bp product; Primer 1/Primer 2, a 500-bp PCR product; Primer 2/Primer 4, a 1080-bp product; Primer 2/Primer 3, a 2240-bp product; Primer 2/Primer 5, a 4000-bp product.

The PCR protocol for the Primer 0/Primer 2 and Primer 1/Primer 2 combinations is:

1. Soaking at 80° C. for 2–5 min.
2. Denaturing at 94° C. for 1 min.

3. Annealing at 52° C. for 1.5 min.
4. Elongating at 72° C. for 3 min.
5. Final extension at 72° C. for 5 min.
6. Soaking at 4° C. until retrieval.

The PCR protocol for the Primer 2/Primer 4, Primer 2/Primer 3, and Primer 2/Primer 5 combinations is:
1. Soaking at 80° C. for 2–5 min.
2. Denaturing at 94° C. for 1 min.
3. Annealing and elongation at 67° C. for 6 min.
4. Final extension at 67° C. for 5 min.
5. Soaking at 4° C. until retrieval.

After the PCR is completed, a gel [2% agarose, TAE buffer (Tris base, 40 mM; sodium acetate, 20 mM; EDTA, 2 mM), pH 8.3] is run to identify the PCR products with comparison to a known marker. Next the fluorescence of the PCR products is measured by mixing 30–40 $\mu$l sample in 2 ml dye solution [10 $\mu$l of 0.1 $\mu$g/ml Hoechst 33258 solution, 10.0 ml of TNE solution (0.2M NaCl, 10 mM Tris-HCl, 1 mM EDTA, pH 7.4), and 90.0 ml distilled water] and measuring the fluorescence at $\lambda_{exc}$=355 nm and $\lambda_{em}$=450 nm with a spectrophotometer (Perkin Elmer LS3). The fluorescence intensity before PCR is subtracted from the fluorescence intensity after PCR. Calibration is accomplished with the use of calf thymus DNA (1 mg ml$^{-1}$; Hoefer Scientific Instruments, San Francisco, Calif.), diluted to 100 $\mu$g ml$^{-1}$ to normalize for percentage of A-T as compared with the lambda DNA. The fluorescence at $\lambda_{exc}$ 355 nm and $\lambda_{em}$ 450 nm was measured with an LS-3 fluorescence spectrophotometer (Perkin Elmer, Wilton, Conn.). The fluorescence of the PCR mixture before PCR (background fluorescence) was subtracted from the fluorescence of the PCR mixture after PCR.

Spots of solar irradiated 50' and calibration DNA are treated individually to find the amount $A_D$ of amplified segment. The control 50 was used to calculate the average amount $(A_0)_{AVE}$ of amplified segment. The ratio, $A_D/(A_0)_{AVE}$ is plotted in FIG. 2, for which the PCR was performed 16 times. Each PCR experiment with 3 repeats with different amounts of template DNA was repeated at least twice on two different days (N$\geq$6). ($\diamond$) 150; ($\blacksquare$) 100; ($\Delta$) 50; ($\bullet$) 30 ng DNA.

Figure 2:
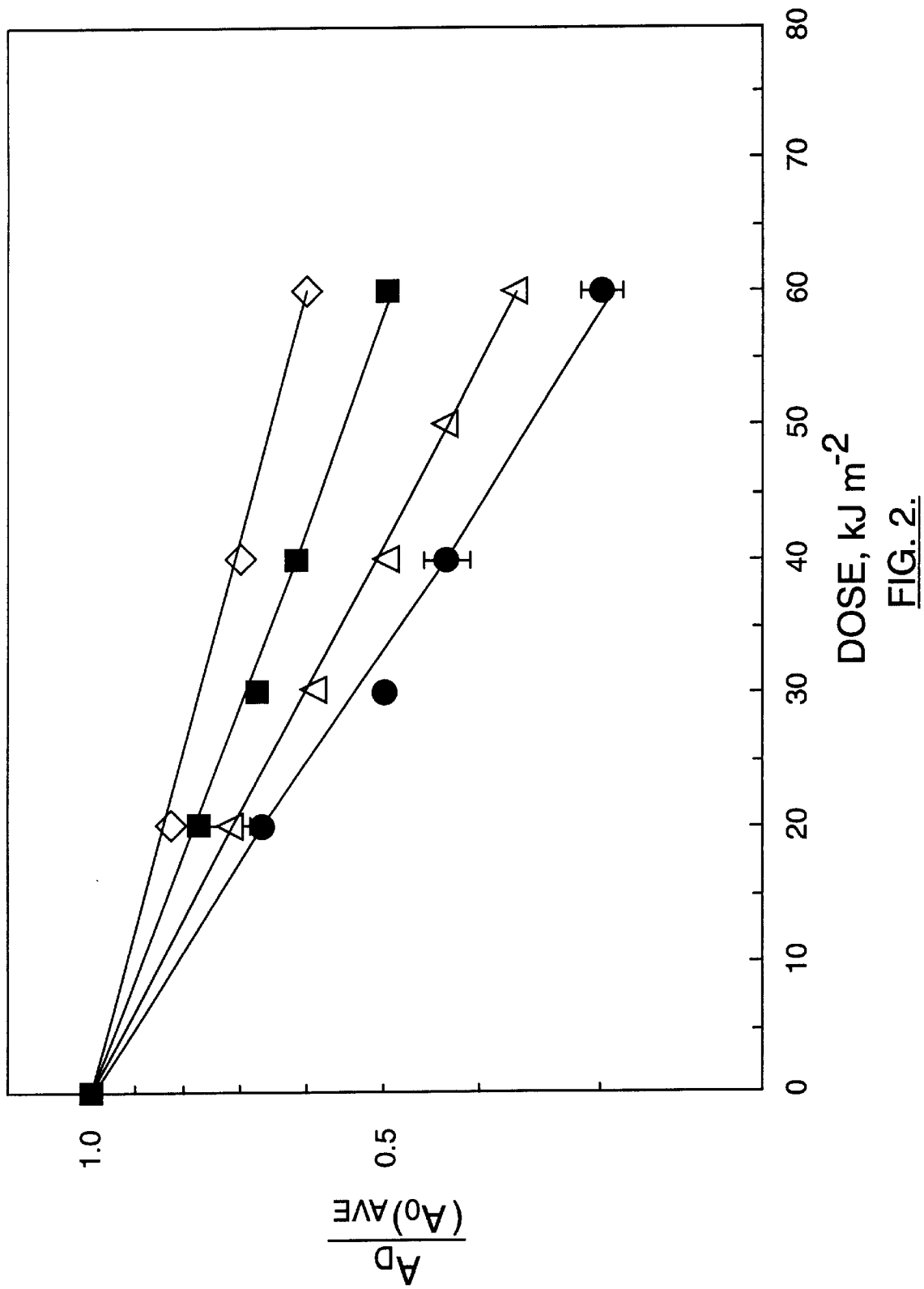
FIG. 2 plots the ratio of the amount $A_D$ of 500-bp segment in UV-exposed, dried DNA to that $(A_0)_{AVE}$ in unexposed, dried DNA as a function of incident dose applied with a solar UVB simulator.
Figure 3C:
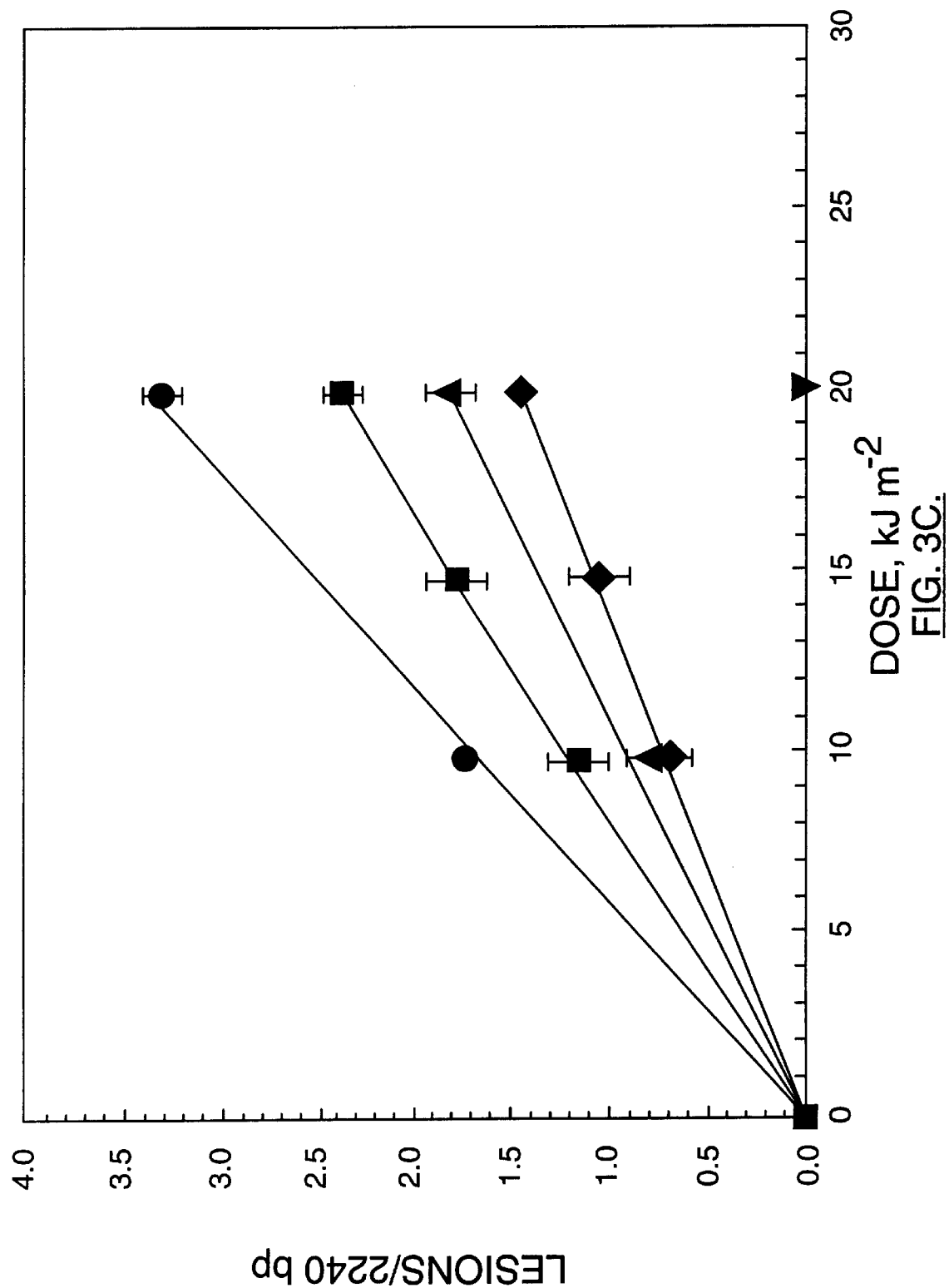
FIG. 3C plots the average lesion frequency as for FIG. 3A, for a 2240-bp segment.

The ratio of FIG. 2 was subjected to a Poisson equation [$-\ln A_D/(A_0)_{AVE}$] to obtain the average lesion frequency per 500 bp per strand for the exposed dosimeters (FIGS. 3A–C). The process is repeated for statistical accuracy.

In FIG. 3A the average lesion frequency for a 500-bp segment is plotted as a function of incident dose applied with a solar UVB simulator for ($\diamond$) 150; ($\blacksquare$) 100; ($\Delta$) 50; ($\bullet$) 30 ng DNA amounts. The average lesion frequency [$-\ln A_D/(A_0)_{AVE}$] is calculated based on the results of FIG. 2.

In FIG. 3B the average lesion frequency for a 1080-bp segment is plotted as for FIG. 3A, for ($\circ$) 25, ($\Delta$) 50, ($\square$) 100, and ($\diamond$) 150 ng dried template DNA. Also shown is the average lesion frequency ($\nabla$) for 50 ng DNA irradiated with a MYLAR covering film.

In FIG. 3C the average lesion frequency for a 2240-bp segment is plotted as for FIG. 3A, for ($\bullet$) 25, ($\blacktriangle$) 50, ($\blacksquare$) 100, and ($\blacklozenge$) 150 ng dried template DNA. Also shown is the average lesion frequency ($\blacktriangledown$) for 50 ng DNA irradiated with a MYLAR covering film.

Results of the Dosimeter Analysis

The amount of amplified product in dried DNA has been found to be substantially identical to that in aqueous DNA for the same amount of unirradiated DNA. This indicates that manipulation of the DNA, such as rehydration of dried DNA and transfer of the rehydrated DNA solution from the film to the PCR tubes, does not have any effect on the amplification efficiency. As long as the concentration of primers, Mg$^{2+}$ ions in the PCR buffer, dNTP and the PCR cycles and the pH of the buffer were controlled and fixed, the PCR assay was reproducible.

Since the effect of self-shielding on dried DNA has not been known in the art, four different concentrations of DNA were prepared before drying the DNA. The same volume (5 $\mu$l) was applied onto the films to obtain 30, 50, 100, and 150 ng of DNA. Although the concentrations of the solution were different, the diameter of the DNA solution spotted onto a film was essentially the same (~2.5 mm) irrespective of the concentration. The ratio $A_D/(A_0)_{AVE}$ of amplified product was plotted as a function of dose for the four different initial amounts of template DNA applied onto the film (FIG. 2). Since any lesion induced by UV irradiation blocks the polymerase from synthesizing the new amplification segment, the amount of amplified product decreases with increasing dose. All four dosimeters with the four different amounts of DNA exhibited a single exponential decay over the range of doses investigated. The amount of amplified product was reduced by ~70% for 30 ng of template DNA, whereas the amount was reduced by ~40% for 150 ng of template DNA at 60 kJ m$^{-2}$.

The average lesion frequency induced by the solar UVB simulator in the 500-, 1080-, and 2240-bp segments per strand was plotted as a function of dose for four different amounts of DNA (FIGS. 3A–C, respectively). The average lesion frequency increases linearly with increasing dose. However, the slope with the smaller amount of dried DNA was greater than that with the larger amount of DNA, showing that the average lesion frequencies decrease as the amount of DNA increases per dose (Table 2).

Figure 4:
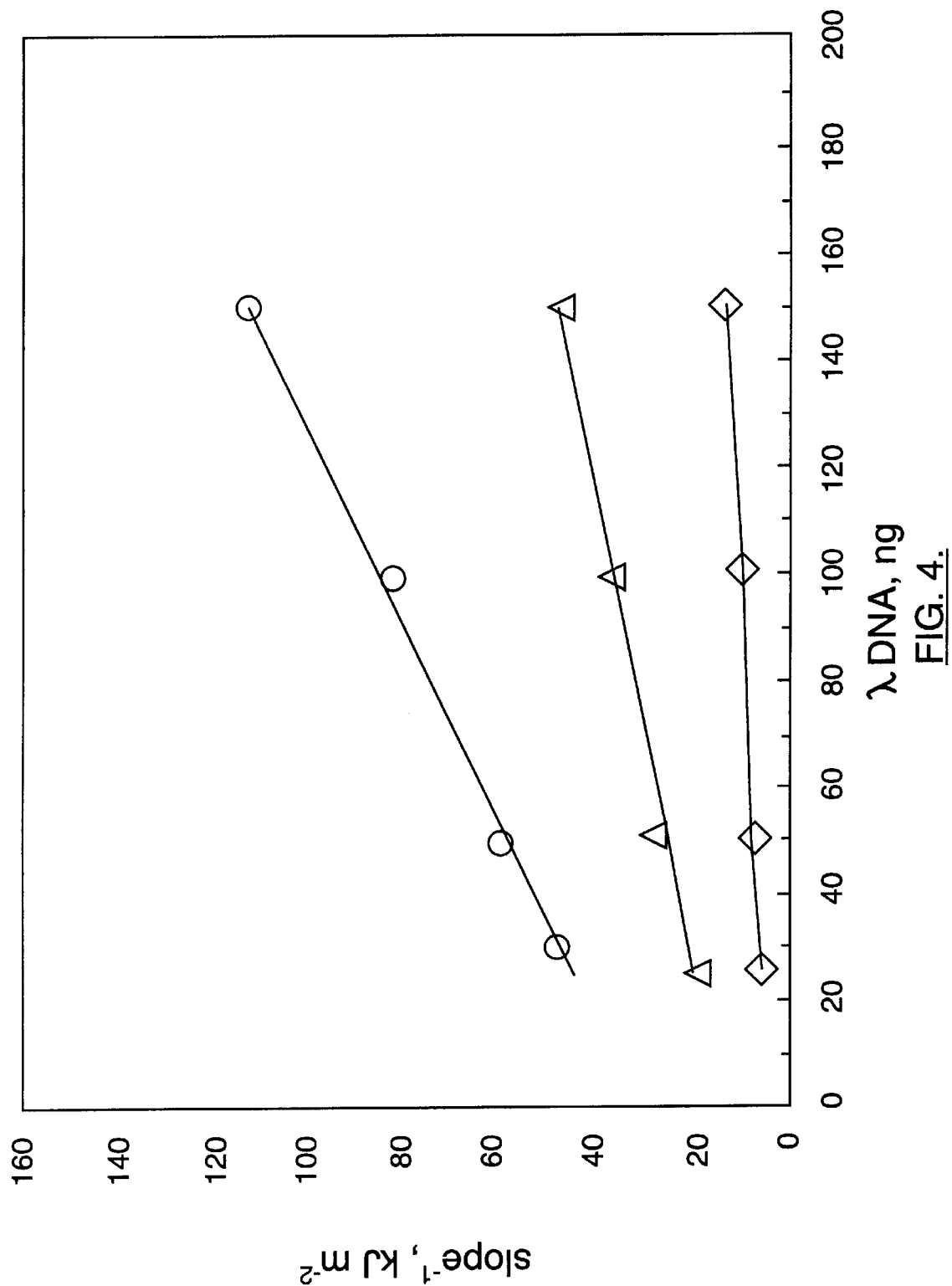
FIG. 4 plots the inverse of the slopes of FIG. 3A (500 bp, ○), FIG. 3B (1080 bp, ∆), and FIG. 3C (2240 bp, ◊) in kJ $m^{-2}$ as a function of the initial amount of template DNA.

The effect of the initial amount of DNA on the lesion frequency was further investigated by plotting the inverse of the slopes of FIGS. 3A–C, shown in FIG. 4. The slopes in FIG. 4, in kJ m$^{-2}$, represent the incident doses to induce one lesion in a 500-, 1080-, or 2240-bp segment for each amount of DNA. This result indicates that this quantity increases linearly as a function of the initial amount of template DNA in the range studied.

Figure 5:
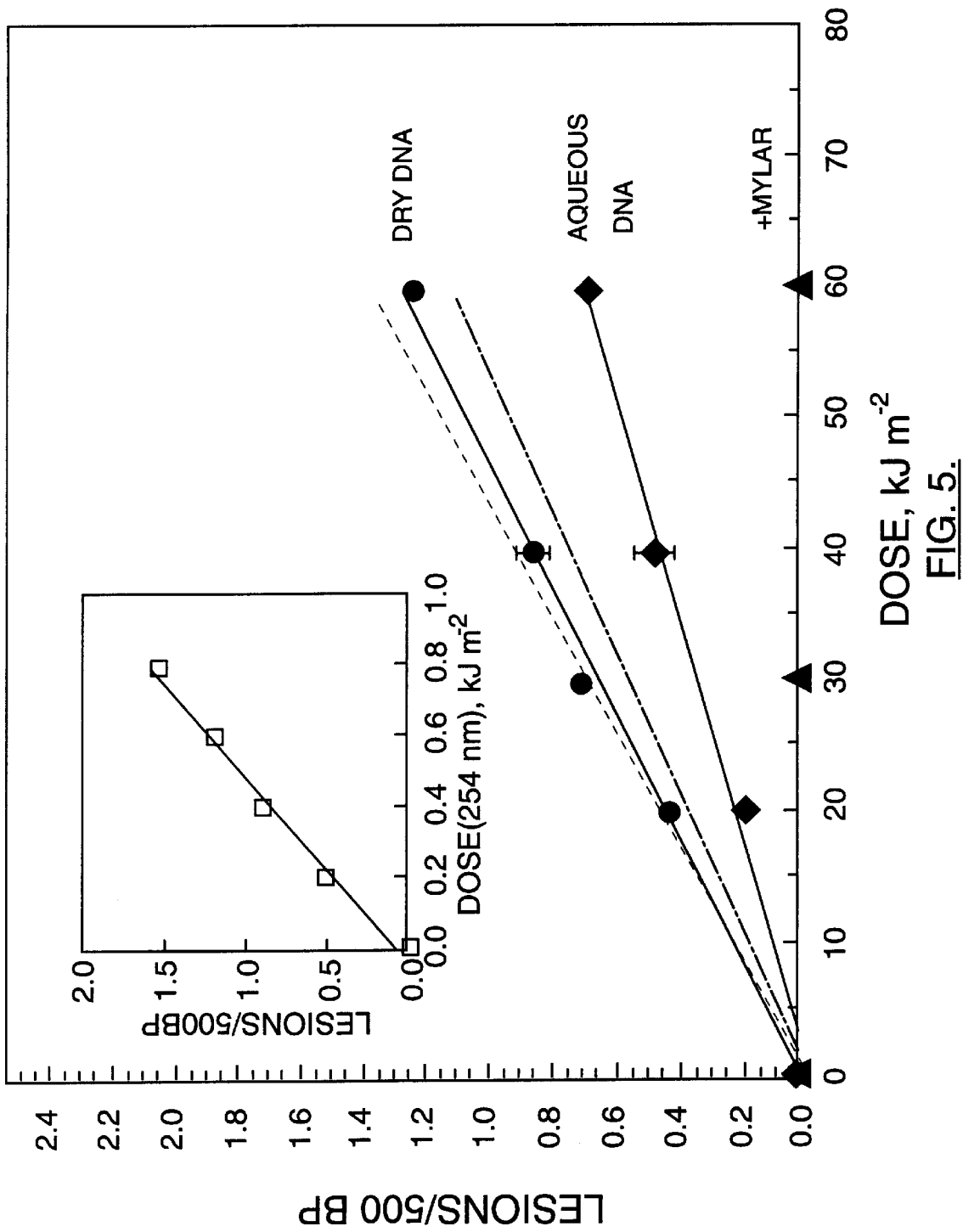
FIG. 5 plots the average lesion frequency as a function of incident dose for several forms of DNA.
Figure 6:
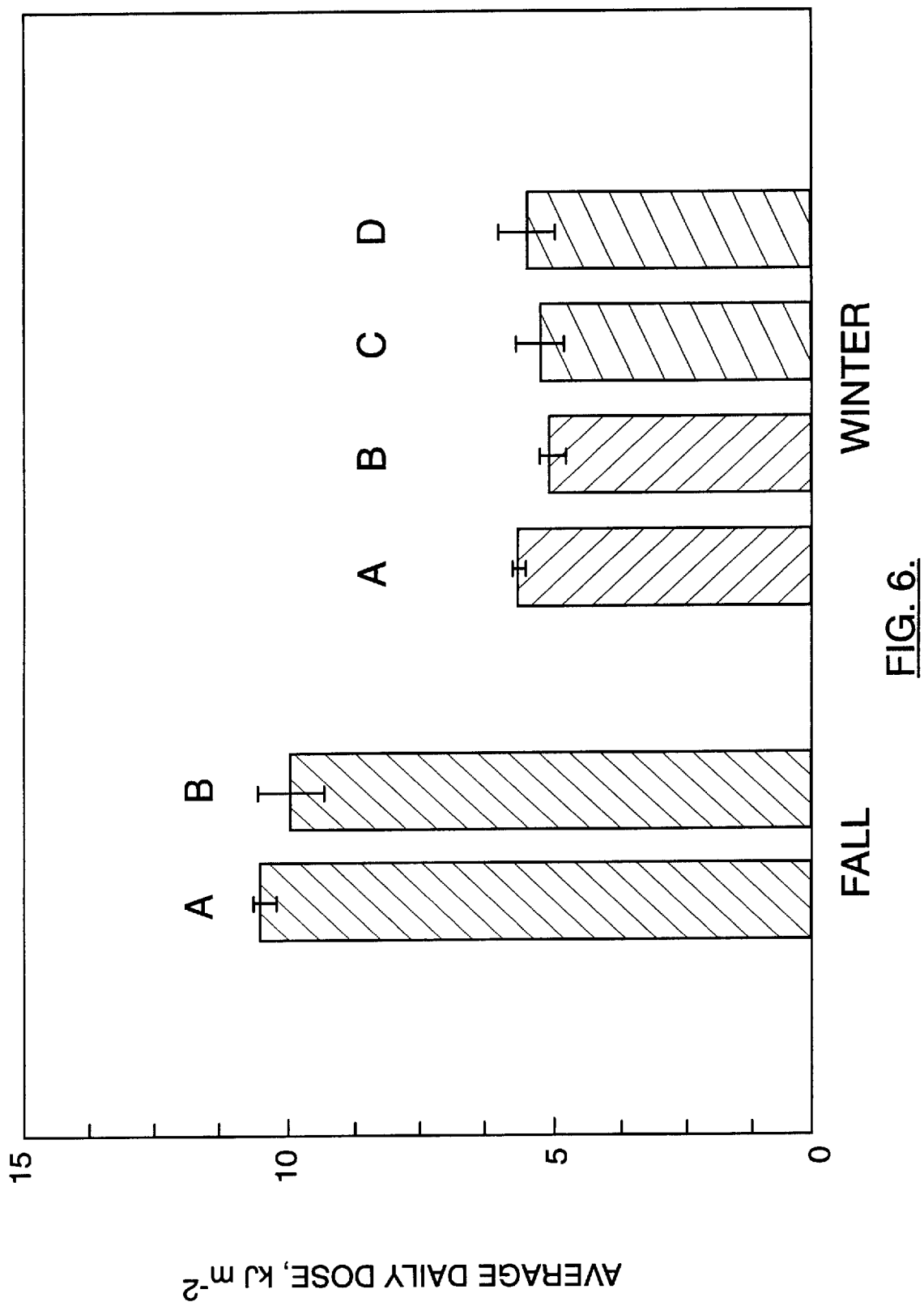
FIG. 6 plots the average daily dose for the fall (shaded bars) and winter (solid and hatched bars) exposures. A and B: 50-ng dosimeters; C and D, 150 ng dosimeters.
Figure 7A:
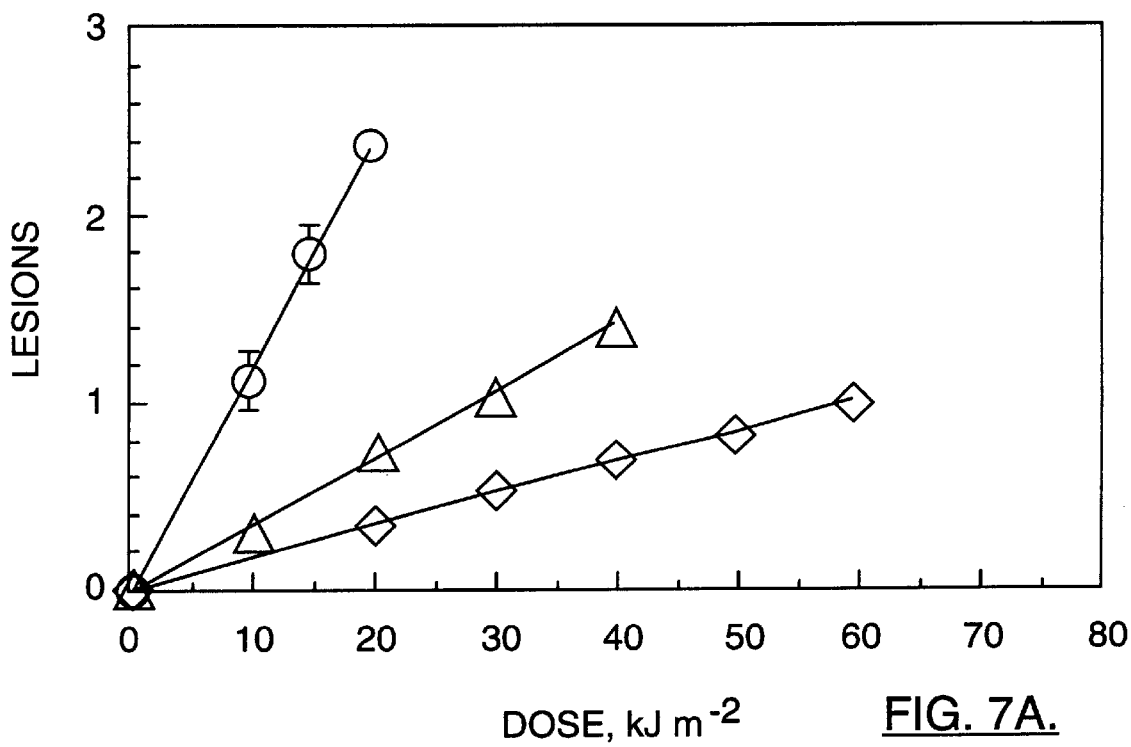
FIGS. 7A and B plot the average lesion frequency for (◊,♦) 500-, (∆,▲) 1080-, and (○,●) 2240-bp amplified product with (A) 50 and (B) 100 ng of template DNA.
Figure 7B:
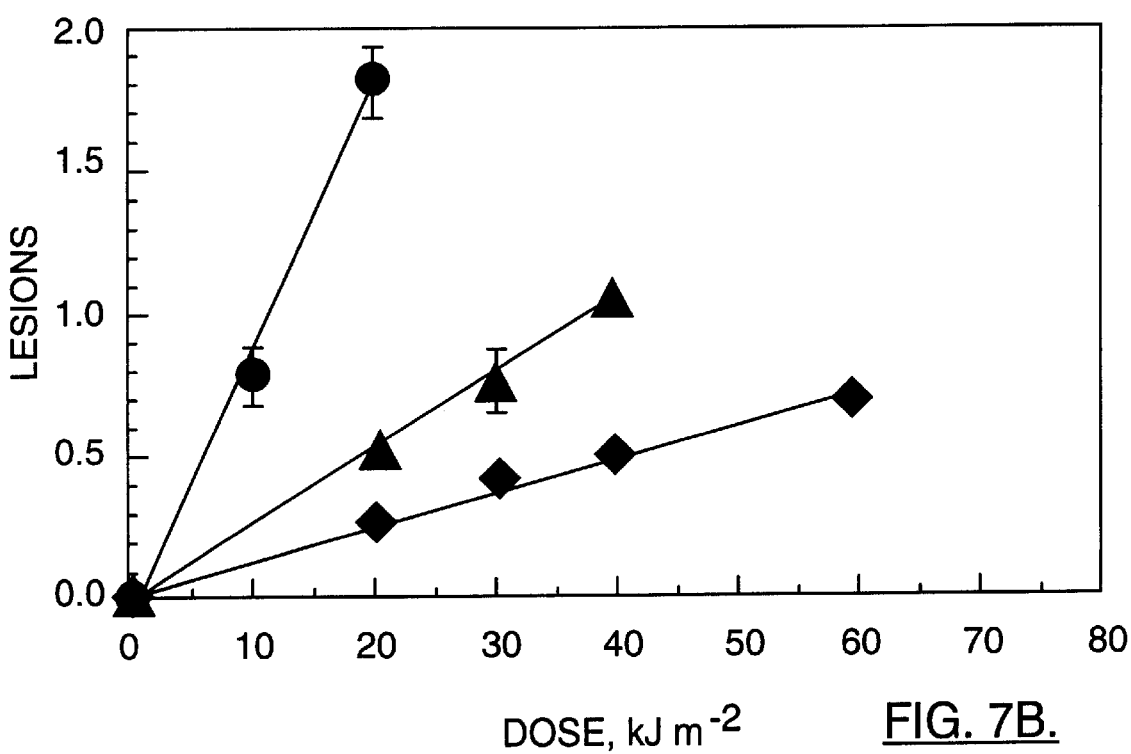

The lesion frequency in the 500-bp segment with dried DNA was compared with that for aqueous DNA, both of which were irradiated with the solar UVB simulator. In FIG. 5 is plotted the average lesion frequency for dried DNA ($\bullet$), aqueous DNA ($\blacklozenge$), and dried DNA covered with MYLAR film ($\blacktriangle$) irradiated as a function of incident dose applied with the solar UVB simulator. The amount of dried DNA was 30 ng at 16 PCR cycles. The concentration of aqueous DNA was 5 ng $\mu$l$^{-1}$. The inset indicates an average lesion frequency for aqueous DNA solution irradiated with a germicidal lamp ($\square$). The slope (absorption cross section) for dried DNA is corrected by multiplying by a factor of 0.94 to correct for shielding (- - -). That for aqueous DNA is corrected by multiplying by a factor of 0.6 (— - —). The concentration of aqueous DNA was 5 ng $\mu$l$^{-1}$ and the amount to DNA analyzed by PCR was 30 ng, as was the dried DNA.

TABLE 2

Summary of Standard Dosimetry Curves for 500 bp, 1080 bp
and 2240 bp with Four Different Amounts of Dried Λ DNA

| Amount of ΛDNA | Number of Lesions* | | | Absorption Cross-Section (m² kJ⁻¹) | | | Dose/One Lesions (kJ m⁻²) | | |
|---|---|---|---|---|---|---|---|---|---|
| | 500bp* | 1080bp** | 2240bp*** | 500bp# | 1080bp+ | 2240bp§ | 500bp# | 1080bp+ | 2240bp§ |
| 25 ng | 1.33 | 1.90 | 3.30 | $2.20 \times 10^{-2}$ | $4.9 \times 10^{-2}$ | $16.5 \times 10^{-2}$ | 45.0 | 20.4 | 6.1 |
| 50 ng | 1.00 | 1.39 | 2.37 | $1.67 \times 10^{-2}$ | $3.5 \times 10^{-2}$ | $11.9 \times 10^{-2}$ | 60.0 | 28.8 | 8.4 |
| 100 ng | 0.70 | 1.05 | 1.80 | $1.20 \times 10^{-2}$ | $2.6 \times 10^{-2}$ | $9.0 \times 10^{-2}$ | 83.3 | 38.1 | 11.1 |
| 150 ng | 0.50 | 0.82 | 1.40 | $0.88 \times 10^{-2}$ | $2.1 \times 10^{-2}$ | $7.0 \times 10^{-2}$ | 114.0 | 48.8 | 14.3 |

*The average number of lesions at 60 kJ m⁻².
**The average number of lesions at 40 kJ m⁻².
***The average number of lesions at 20 kJ m⁻².
From FIG. 3A.
+ From FIG. 3B.
§ From FIG. 3C.

This indicates that all the lesions that block the polymerase from synthesizing a new strand in a target segment were about twice as frequent in dried DNA as in the aqueous DNA, assuming that the doses absorbed by DNA through dried and aqueous DNA are the same.

The effect of the germicidal lamp has been compared with that of the solar UVB simulator in producing the UV-induced lesions. The solar UVB simulator was about 200 times less effective in producing lesions than the germicidal lamp (FIG. 5). UV irradiation at 315 nm is known to be about $10^4$ times less effective in producing the DNA damage and killing *E. coli* than at 254 nm.

The average lesion frequency induced by UV above 315 nm was investigated by filtering out the UV radiation below 315 nm using a layer of MYLAR film. The amount of amplified product in irradiated DNA for 60 kJ m⁻² was the same as that in unirradiated DNA. Thus the average lesion frequency per 500-bp strand was nil at 60 kJ m⁻², as shown in FIG. 5. Any photoinduced damage in DNA induced by UVA (320–400 nm) apparently does not affect the amplification of the 500-bp segment in the doses tested. Thus the dosimeter of the present invention appears to truly represent a UVB dosimeter.

The UV dosimeters encased in their housings were placed outdoors for 4 continuous days. The first set (two dosimeters, A and B, each containing 50 ng of λ DNA) was placed outdoors in the fall in Melbourne, Fla. (Table 3). During this time interval there was sunlight with some patches of clouds each day, but there was rain in the evening (17:30–19:00) on the second day ($T_{high}$=35° C., $T_{low}$=20° C.). The total 4-day day-dose was 39.5–41.6 kJ m⁻², with the average daily dose of 9.9–10.4 kJ m⁻². The second set (two dosimeters, each containing 50 ng λ DNA, A and B; and two dosimeters, each containing 150 ng λ DNA, C and D) was placed in the same location as the first set, over four days in the winter. The weather at that time was clear and sunny ($T_{high}$=10° C., $T_{low}$=0° C.), but it rained in the morning and became cloudy in the afternoon of the fourth day. The total 4-day dose for that period was 19.9–22.2 kJ m⁻², with the average daily dose of 5.0–5.5 kJ m⁻² with the 50-ng dosimeter. The total 4-day dose for that period was 20.4–21.3 kJ m⁻², with the average daily dose of 5.1–5.3 kJ m⁻² with the 150-ng dosimeter. Both dosimeters recorded essentially the same dose, although the lesion frequencies were very different (Table 3 and FIG. 6). Thus the average daily dose was found to be ~10.2±0.4 kJ m⁻² for the fall test and ~5.2±0.3 kJ m⁻² for the winter test.

TABLE 3

Summary of Four-Day Dosimetry

| Exposed* | Type of Dosimeter | Number of Lesions** | Total 4-Day Dose (kJ m⁻²) | Average Daily Dose (kJ m⁻²) |
|---|---|---|---|---|
| Fall | A. (50 ng) | 0.694 ± 0.015 | 41.6 ± 0.9 | 10.4 ± 0.2 |
| | B. (50 ng) | 0.659 ± 0.041 | 39.5 ± 2.5 | 9.9 ± 0.6 |
| | A. (50 ng) | 0.369 ± 0.007 | 22.2 ± 0.4 | 5.5 ± 0.1 |
| | B. (50 ng) | 0.332 ± 0.014 | 19.9 ± 0.8 | 5.0 ± 0.2 |
| | C. (150 ng) | 0.179 ± 0.015 | 20.4 ± 1.8 | 5.1 ± 0.4 |
| | D. (150 ng) | 0.186 ± 0.018 | 21.3 ± 2.1 | 5.3 ± 0.5 |

*Started and ended at 5 PM of the day.
**The average lesion frequency per 500 bp per strand.

A and B dosimeters for the fall and the winter tests, both of which contained 50 ng of DNA, were prepared from the same DNA solutions and dried at the same time. The amount of amplified product for the control used in the fall and winter was 0.72±0.002 and 0.78±0.04 mg, respectively, after 16 cycles. A year-old dosimeter also produced the same amount of the amplified segment within experimental error (0.77±0.04 mg). Considering the different batches of PCR reagents used on two different assays, these numbers are well within experimental error, indicating the stability of the dosimeter of the present invention over at least a one-year shelf time.

Two different dosimeters were also positioned for time spans of 1, 2, and 4 days, one having 50 ng and the other having 100 ng λ DNA per spot. The PCR analysis was then carried out with 2240 bp for the 1-day exposure, 1080 bp for the 2-day exposure, and 500 bp for the 4-day exposure, the results of which are given in Table 4. The 4-day doses of UVB based on the 1080- and 2240-bp amplification were within experimental error and agreed with the total 4-day dose obtained with the 500-bp amplification.

It is believed that the principal mechanism of the PCR with irradiated DNA is that photoinduced lesions block the new synthesis of amplified segments. The average lesion frequency per strand for each amount of initial template DNA increases approximately linearly with increasing dose and decreases with the amount of initial template DNA applied to the film. The surface area of spots is ~5×10⁻⁶ m² and is independent of the initial amount of template DNA applied. The only difference among these dosimeters is the concentration of solution before being dried; therefore, the important parameter appears to be the number of molecules present after being dried (Table 2). In dried DNA, the DNA molecules stack upon each other as the amount the DNA increases, which causes a shielding of the molecules below the top few layers; therefore, the probability of a molecule below the top few layers interacting with a photon is very small. The average lesion frequency with a 150-ng dosimeter was approximately half that with a 25-ng dosimeter per dose, since the undamaged molecules protected by the top molecules contributed more to the formation of amplified segment. This effect is also plotted in FIGS. 7A and 7B, wherein the average lesion frequency for 500-, 1080-, and 2240-bp segments is plotted against dose for (FIG. 7A) 50 ng and (FIG. 7B) 100 ng of template DNA.

they can be used for a month. An important feature of the present invention is the use of a nucleic acid molecule, in the preferred embodiment λ DNA, the entire sequence of which is known. Certain portions of the DNA of different sizes can be created by choosing specific primers, which in turn provides a dosimetry for different exposure times. By also factoring in an initial amount of template DNA present in each spot, a virtually continuous range of dosimeters can be constructed and analyzed. As an example, the three segment sizes discussed herein (500, 1080, and 2240 bp) in combination with four different amounts of DNA (e.g., 25, 50, 100, and 150 ng), provides twelve different dosimeters, from

TABLE 4

Summary of Four-Day Dosimetry

| | 50 ng λDNA | | | 100 ng λDNA | | |
|---|---|---|---|---|---|---|
| Dates | Average Lesions* | Total Dose (kJ m$^{-2}$) | Dose/Day (kJ m$^{-2}$) | Average Lesions* | Total Dose (kJ m$^{-2}$) | Dose/Day (kJ m$^{-2}$) |
| A. 2240 bp Amplification for One-Day Dosimetry | | | | | | |
| Day 1–2 | 0.629 ± 0.072 | 5.3 ± 0.6 | 5.3 | 0.513 ± 0.071 | 5.5 ± 0.9 | 5.5 |
| Day 2–3 | 0.577 ± 0.082 | 5.0 ± 0.6 | 5.0 | 0.536 ± 0.065 | 6.0 ± 0.7 | 6.0 |
| Day 3–4 | 0.636 ± 0.017 | 5.4 ± 0.1 | 5.4 | 0.483 ± 0.066 | 5.4 ± 0.7 | 5.4 |
| Day 4–5 | 0.435 ± 0.025 | 3.7 ± 0.2 | 3.7 | 0.343 ± 0.022 | 3.8 ± 0.3 | 3.8 |
| B. 1080 bp Amplification for Two-Day Dosimetry | | | | | | |
| Day 1–3 | 0.374 ± 0.075 | 10.8 ± 2.2 | 5.4 | 0.282 ± 0.035 | 10.8 ± 1.3 | 5.4 |
| Day 3–5 | 0.309 ± 0.049 | 8.9 ± 1.4 | 4.5 | 0.262 ± 0.027 | 10.0 ± 1.0 | 5.0 |
| C. 500 bp Amplification for Four-Day Dosimetry | | | | | | |
| Day 1–5 | 0.350 ± 0.02 | 21.0 ± 1.4 | 5.3 | 0.254 ± 0.04 | 20.9 ± 3.3 | 5.2 |

*Average number of lesions per 2240 bp, 1080 bp, and 500 bp per strand for A, B, and C, respectively.

A calculation of an amount of DNA at which shielding begins has been performed. Since this DNA is ~200 nm long and ~50 nm wide (icosahedral head plus tail), a single molecule takes up ~0.01 $\mu m^2$. This implies that there are ~100 molecules in a 1 $\mu m^2$ area. Thus there are ~5×10$^8$ molecules of DNA, corresponding to an amount of ~25 ng in a spot of 5×10$^{-6}$ m$^2$. By extrapolating the slope of FIG. 4 at 25 ng, the average lesion frequency was found to be ~1.33. This is believed to represent the maximum number of lesions obtainable for the 500-bp segment with a dose of 60 kJ m$^{-2}$.

It is known that a percent survival of organisms subjected to radiation depends upon the material irradiated and the thickness of the material. A correction factor was found based upon the standard single-hit target theory. By multiplying the light intensities incident upon the surface by a correction factor, one can calculate the dose necessary to find the same inactivation if the organism were spread in a single layer on a surface. The correction factor for the efficiency of amplification of the specific segment of dried λ DNA was found using the same analogy (Table 2). Correction factors for the average dose through dried DNA were found to be ~0.94, 0.76, 0.55, and 0.40 for 30, 50, 100, and 150 ng DNA for amplification of the 150-ng segment, respectively.

Dried DNA on a film such as that disclosed herein is easier to control than aqueous DNA, although both in principle are usable as UVB dosimeters.

An advantage of the DNA dosimeter of the present invention comprises an inherent dynamic versatility for short- and long-term measurements. Some biological dosimeters that are known in the art are so sensitive that they can be used for only a 1-min exposure, or are so insensitive that which it can be seen that a dosimeter could be tailored for specific exposure times. That is, a shorter-base-pair product would be preferable for longer exposure times, as the slope in FIG. 2 is shallower; and conversely for longer-base-pair products. Exemplary base-pair products for desired exposure times are listed in Table 5.

TABLE 5

Exposure Time Ranges for Various Sizes of Base-Pair Products

| Base-Pair Product Size (bp) | Exposure Time |
|---|---|
| 230 | 2 weeks–1 month |
| 500 | 4 days–2 weeks |
| 1080 | 2–8 days |
| 2240 | 1–4 days |
| 4000 | 1–6 hours |

The dosimeter and method of the present invention are seen to accomplish the stated goals of providing an inexpensive, small, portable device suitable for personal use. The device can be constructed so as to be impervious to extremes of environmental conditions and to be usable underwater.

Additionally, the invention provides an accurate measure of radiation dosage within a specific, predetermined wavelength range that has a builtin control sample and can be used for a wide range of times (typically over a number of days, although this is not meant to be limiting). As the dosimeter is biomolecular, only biologically effective doses are measured, which are considered valuable under a wide array of conditions.

It may be appreciated by one skilled in the art that additional embodiments may be contemplated, including other dosimeter structures for alternative applications and the use of analogous biological macromolecules as radiation dosimeters for other ranges of incident wavelengths.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the device and method illustrated and described herein are by way of example, and the scope of the invention is not limited to the exact details of construction and analysis.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

SEQUENCE LISTING

<160> 10

<210> 1
<211> 26
<212> DNA
<213> Artificial Sequence

<220>
<223> Description of Artificial Sequence:230 BP
(7401-7630) Primer 2

<400> 1
ggttatcgaa atcagccaca gcgcct                                              26

<210> 2
<211> 25
<212> DNA
<213> Artificial Sequence

<220>
<223> Description of Artificial Sequence:230 bp
(7401-7630) Primer 0

<400> 2
tgggatcagc gcagccggat accgt                                               25

<210> 3
<211> 25
<212> DNA
<213> Artificial Sequence

<220>
<223> Description of Artificial Sequence:500 bp
(7131-7630) Primer 2

<400> 3
ggttatcgaa atcagccaca gcgcc                                               25

<210> 4
<211> 25
<212> DNA
<213> Artificial Sequence

<220>
<223> Description of Artificial Sequence:500 bp
(7131-7630) Primer 1

<400> 4
gatgagttcg tgtccgtaca actgg                                               25

<210> 5
<211> 25
<212> DNA
<213> Artificial Sequence

<220>
<223> Description of Artificial Sequence:1080 bp
(6551-7630) Primer 2

<400> 5

-continued

```
ggttatcgaa atcagccaca gcgcc                                                    25

<210> 6
<211> 25
<212> DNA
<213> Artificial Sequence

<220>
<223> Description of Artificial Sequence:1080 bp
      (6551 - 7630) Primer 4

<400> 6
atacaccatg accggtgaag ccttc                                                    25

<210> 7
<211> 25
<212> DNA
<213> Artificial Sequence

<220>
<223> Description of Artificial Sequence:2240 bp
      (5391 - 7630) Primer 2

<400> 7
ggttatcgaa atcagccaca gcgcc                                                    25

<210> 8
<211> 25
<212> DNA
<213> Artificial Sequence

<220>
<223> Description of Artificial Sequence:2240 bp
      (5391 - 7630) Primer 3

<400> 8
ctgacgttac tgacgtggtg ccagc                                                    25

<210> 9
<211> 26
<212> DNA
<213> Artificial Sequence

<220>
<223> Description of Artificial Sequence:4000 bp
      (3631 - 7630) Primer 2

<400> 9
ggttatcgaa atcagccaca gcgcct                                                   26

<210> 10
<211> 25
<212> DNA
<213> Artificial Sequence

<220>
<223> Description of Artificial Sequence:4000 bp
      (3631 - 7630) Primer 5

<400> 10
aacacgcagc tgcagagcgc cattg                                                    25
```

That which is claimed is:

1. A dosimeter for measuring a radiation dosage in a predetermined ultraviolet (UV) wavelength range comprising:

a housing;

a first supporting structure positioned in said housing;

a quantity of desiccated detection DNA adhered to a first side of the first supporting structure, the desiccated detection DNA comprising a known number and sequence of base pairs and having a vulnerability to radiation in the predetermined UV wavelength range;

a second supporting structure positioned adjacent the first supporting structure in said housing;

a quantity of desiccated control DNA adhered to a first side of the second supporting structure, the desiccated control DNA having a known number and sequence of base pairs; and at least one shield in said housing and positioned to protect the control DNA from impinging radiation, the at least one shield blocking radiation in the predetermined UV wavelength range;

said housing providing physical protection for the desiccated detection DNA and the desiccated control DNA while exposing the detection DNA to radiation in the predetermined UV wavelength range to produce quantifiable damage thereto indicative of radiation dosage.

2. The dosimeter recited in claim 1, further comprising:

a first covering sheet positioned in covering relation to the desiccated detection DNA and affixed to the first side of the first supporting structure; and a second covering sheet positioned in covering relation to the desiccated control DNA and affixed to the first side of the second supporting structure with the second covering sheet being adjacent the first supporting structure;

the first and second covering sheets for further protecting the detection DNA and the control DNA from physical damage.

3. The dosimeter recited in claim 2, wherein said housing comprises means for creating a fluid-impervious seal between the first supporting structure and the first covering sheet and between the second supporting structure and the second covering sheet, for permitting the dosimeter to be used in an aqueous environment.

4. The dosimeter recited in claim 2, wherein the first and the second covering sheets each comprises a plastic film transparent to radiation in the predetermined UV wavelength range.

5. The dosimeter recite in claim 4, wherein the first and second supporting structures each comprises a plastic film transparent to radiation in the predetermined UV wavelength range.

6. The dosimeter recited in claim 5, wherein said housing further comprises a silicone sealant applied in moisture-impervious sealing relation to the first supporting structure and the first covering sheet and to the second supporting structure and the second covering sheet, for permitting the dosimeter to be used in an aqueous environment.

7. The dosimeter recited in claim 1, wherein the housing comprises a moisture-impervious housing, for permitting the dosimeter to be used in an aqueous environment.

8. The dosimeter recited in claim 1, further comprising means for affixing said housing to a subject, the affixing means positioned to permit the desiccated detection DNA to receive the same dosage of impinging radiation as the subject.

9. The dosimeter recited in claim 1, wherein:

the desiccated detection DNA comprises a plurality of measured quantities of desiccated DNA disposed in spaced relation from each other atop the first supporting structure; and the desiccated control DNA comprises a plurality of measured quantities of desiccated DNA disposed in spaced relation from each other atop the second supporting structure.

10. The dosimeter recited in claim 1, wherein the desiccated detection DNA and the desiccated control DNA each comprise a lambda DNA comprising a known number of base pairs and a known sequence thereof.

11. The dosimeter recited in claim 1, wherein the first and the second supporting structures each comprises a plastic film transparent to radiation in the predetermined UV wavelength range.

12. The dosimeter recited in claim 1, further comprising an indicator positioned adjacent the first supporting structure transformable between an unexposed state presenting a first visual appearance and an exposed state presenting a second visual appearance when subjected to radiation in the predetermined wavelength range.

13. The dosimeter recited in claim 1, further comprising an indicator positioned on said housing and being transformable between an unexposed state presenting a first visual appearance and an exposed state presenting a second visual appearance when subjected to radiation in the predetermined UV wavelength range.

14. A method for measuring a radiation dose within a predetermined ultraviolet (UV) wavelength range using a DNA dosimeter, the method comprising the steps of:

exposing a known quantity of desiccated detection DNA of the DNA dosimeter to an environment for a measured time span, the desiccated detection DNA being vulnerable to radiation in the predetermined UV wavelength range and comprising a known number and sequence of base pairs;

amplifying a region of the exposed desiccated detection DNA;

determining a lesion frequency within the exposed desiccated detection DNA from the amplified exposed desiccated detection DNA region; and determining a dose of radiation experienced by the desiccated detection DNA within the predetermined UV wavelength range from a comparison of the lesion frequency with a set of predetermined dose-response calibration data.

15. The method recited in claim 14, further comprising the step of performing a control measurement for ensuring that the determined radiation dose represents a measurement based upon the exposure to the environment.

16. The method recited in claim 15, wherein the control measurement performing step comprises the steps of:

exposing a known quantity of shielded desiccated control DNA to the environment for the measured time span simultaneously with the desiccated detection DNA, the shielded desiccated control DNA having a known number and sequence of base pairs;

amplifying a region of the exposed shielded desiccated control DNA corresponding to the amplified desiccated detection DNA region;

determining a lesion frequency within the exposed shielded desiccated control DNA from the amplified exposed shielded desiccated control DNA region; and determining a dose of radiation experienced by the shielded desiccated control DNA within the predetermined UV wavelength range from a comparison of the lesion frequency therein with the predetermined set of dose-response data.

17. The method recited in claim 14, wherein the amplifying step comprises performing a polymerase chain reaction assay.

18. The method recited in claim 14, wherein the lesion frequency determining step comprises adding a tracer to the amplified exposed shielded desiccated control DNA and quantifying products of the polymerase chain reaction assay by detecting a quantity of tracer.

19. The method recited in claim 18, wherein the tracer adding step comprises adding a fluorescent dye.

20. The method recited in claim 19, wherein the product quantifying step comprises running a gel with the products and quantifying a series of bands thereon.

21. A method of making a dosimeter for measuring a radiation dose within a predetermined wavelength range comprising the steps of:

adhering a first quantity of desiccated detection DNA to a first side of a first supporting structure, the desiccated detection DNA comprising a known number and sequence of base pairs and having a vulnerability to radiation in the predetermined UV wavelength range;

adhering a second quantity of desiccated control DNA to a first side of a second supporting structure, the desiccated control DNA having a known number and sequence of base pairs;

positioning at least one shield in protection relation to the desiccated control DNA to shield the desiccated control DNA from impinging radiation, the at least one shield blocking radiation in the predetermined UV wavelength range; and packaging the first supporting structure and the shielded second supporting structure into a housing for providing physical protection for the desiccated detection DNA and the desiccated control DNA while exposing the desiccated detection DNA to radiation in the predetermined UV wavelength range to produce quantifiable damage to the desiccated detection DNA indicative of radiation dosage.

* * * * *